United States Patent [19]
Calder

[11] Patent Number: 6,026,684
[45] Date of Patent: Feb. 22, 2000

[54] ACTIVE DONOR HAND GRIPPER FOR USE IN A BLOOD COLLECTION APPARATUS

[75] Inventor: Greg William Calder, Abington, Mass.

[73] Assignee: Haemonetics Corporation, Braintree, Mass.

[21] Appl. No.: 09/118,416

[22] Filed: Jul. 17, 1998

[51] Int. Cl.$^7$ ..................................................... A61B 1/24
[52] U.S. Cl. ...................................................... 73/379.02
[58] Field of Search .................................... 128/774, 782, 128/DIG. 12, DIG. 13; 73/379.01–379.03; 604/30, 65–67; 340/407.1, 965, 825.19; 434/112, 113, 114

[56] References Cited

U.S. PATENT DOCUMENTS

| | | |
|---|---|---|
| 3,807,729 | 4/1974 | Sigma . |
| 4,114,449 | 9/1978 | Dikeman et al. . |
| 4,262,898 | 4/1981 | Lee . |
| 4,425,114 | 1/1984 | Schoendorfer et al. . |
| 4,433,364 | 2/1984 | Noble . |
| 4,498,983 | 2/1985 | Bilstad et al. . |
| 4,530,496 | 7/1985 | Smith et al. . |
| 4,558,864 | 12/1985 | Medwedeff . |
| 4,623,141 | 11/1986 | Salvino . |
| 4,651,987 | 3/1987 | Day . |
| 4,711,445 | 12/1987 | Whitehead . |
| 4,715,849 | 12/1987 | Gion et al. . |
| 4,883,462 | 11/1989 | Williamson et al. .................. 604/66 X |
| 4,884,445 | 12/1989 | Sadoff et al. . |
| 4,943,047 | 7/1990 | Noble . |
| 5,045,057 | 9/1991 | Van Driessche et al. ............ 604/67 X |
| 5,222,926 | 6/1993 | Eggen . |
| 5,451,924 | 9/1995 | Massimino et al. .................. 340/407.1 |
| 5,619,180 | 4/1997 | Massimino et al. .................. 340/407.1 |
| 5,643,138 | 7/1997 | Huang . |
| 5,681,993 | 10/1997 | Heitman ............................... 73/379.02 |

Primary Examiner—Benjamin R. Fuller
Assistant Examiner—Jewel V. Thompson
Attorney, Agent, or Firm—Cesari and McKenna, LLP

[57] ABSTRACT

An active hand gripper for use in a blood drawing apparatus provides a tactile signal to a blood donor reminding the donor to periodically squeeze the hand gripper, thereby increasing donor venous pressure and the related blood flow rate from the donor into the blood drawing apparatus. The tactile signal may be generated, for example, in response to a measured decrease in line pressure; or in response to a projected decrease in line pressure based on analysis of current and past flow parameters; or at pre-set intervals based on a target gripping frequency; or based on the donor's pattern of actual gripping. The gripper can be configured for autonomous operation such that the gripper itself contains circuitry for determining when the tactile signal should be issued, or the gripper can receive a trigger signal from a controller within the blood drawing apparatus.

26 Claims, 4 Drawing Sheets

ACTIVE DONOR HAND GRIPPER FOR USE IN A BLOOD COLLECTION APPARATUS

BACKGROUND OF THE INVENTION

Whole human blood includes predominantly three types of specialized cells: red blood cells, white blood cells, and platelets. These cells are suspended in a complex aqueous solution of proteins and other chemicals called plasma. Although in the past blood transfusions have used whole blood, the current trend is to transfuse only those blood components required by a particular patient. This approach preserves the available blood supply and in many cases is better for the patient, since the patient is not exposed to unneeded blood components. Storage lifetimes can also be increased by packaging the individual blood products separately.

The blood components needed for the transfusion are taken from a donor by a process called apheresis in which the desired one, or more, specific components of the whole blood are separated and harvested by a blood-processing machine. The remaining components are returned to the donor. (As used herein, the term "donor" connotes anyone from whom blood is drawn for collection or processing, and can include volunteer donors or medical patients to whom blood collected components are returned.) Typically, an apheresis apparatus has several peristaltic pumps and a number of valves for controlling the direction and duration of blood flow from the donor and through a recirculating separation process. The device provides a separation chamber, having input and output ports, for separating blood components according to their densities. The output port of the separation chamber is in fluid communication with one or more blood component containers that receive the separated blood components. The output put port may be in further fluid communication with the input port through a recirculation pump in order to recirculate less dense blood components and/or plasma. A phlebotomy needle for withdrawing whole blood from the donor is in fluid communication with the apheresis apparatus and an anticoagulant container.

In operation, a "blood collection cycle" or "draw process" begins with the withdrawal, through the phlebotomy needle, of whole blood from a donor. The whole blood is anticoagulated by mixing with anticoagulant drawn from the anticoagulant container, and the anticoagulated whole blood enters the separation chamber through the input port. During the draw process, a separation process separates lower-density components from higher-density components in the separation chamber. The less-dense component(s) is (e.g., plasma, platelets, and white blood cells) are displaced through the output port into the blood component containers. The separation process is then terminated, and the higher-density components (e.g., red blood cells or "RBC") remaining in the separation chamber are diluted with diluent and returned to the donor, or collected as an RBC product. More specifically, a diluent solution is stored in a diluent container in selective fluid communication with the flow path between the input port of the separation chamber and the phlebotomy needle, and the higher-density components remaining in the chamber are drawn out through the inlet port, mixed with diluent from the diluent container and returned to the donor via the phlebotomy needle. The entire apheresis procedure may be repeated with additional draw processes, wherein whole blood is again drawn from the donor and combined with anticoagulant from the anticoagulant container, followed by additional separation processes.

The apheresis procedure described above is merely exemplary. A number of different apheresis procedures are known in the art, and specific apheresis procedures have developed in response to the demand for specific blood components. In particular, the demand for platelet concentrates with low contamination of white blood cells ("WBC"), such as lymphocytes, has grown rapidly with advances in medical science and cancer therapy. Consequently, a number of procedures are now directed toward optimizing the collection of pure platelet concentrate (see for example U.S. Pat. Nos. 5,494,592 and 4,416,654). A blood drawing process may also be used in non-apheresis procedures such as whole blood collection.

While efficient and straightforwardly practiced, these procedures nonetheless exhibit limitations. In particular, a low donor blood flow rate through the phlebotomy needle often prolongs the time for the draw process. For this reason, a donor should periodically squeeze his hand during the draw process in order to maintain adequate venous pressure at the phlebotomy needle site. Failure of the donor to squeeze his hand will frequently result in reduced blood flow and consequent reduction in pump speed, thus increasing the duration of the procedure and negatively affecting the collection process. If the blood flow rate consistently drops below that required by the collection device, the procedure may be terminated in order to prevent health risk to the donor. To effectuate this safety feature, blood collection systems typically include a donor pressure monitor that senses changes in the line pressure and a control system that slows or stops the peristaltic collection pumps in response to decreasing pressure. The resulting conditions are known as "Low Flow" or "No Flow."

In order to avoid Low Flow/No Flow conditions, a donor is typically provided with a hand-held gripping device or hand gripper which the donor should be reminded to squeeze during the draw process. Some blood drawing apparatus also include a visual indicator which responds to decreasing blood flow rates and alerts the donor to squeeze the hand gripper. However, due to lack of proper instruction and/or lack of donor attention to the alert signal, pressure-related interruptions to blood collection continue to prolong blood drawing procedures.

Accordingly, there is a continuing need for a device to reduce procedure times in blood drawing by interacting with the donor in a manner that assures adequate venous pressure for uninterrupted blood flow.

SUMMARY OF THE INVENTION

The present invention addresses the problem of inadequate donor attention to the need for hand gripping by providing a signal which, while neither intimidating nor jarring to the donor, is nonetheless impossible to ignore. In particular, the invention couples a trigger signal to the gripper itself, which can vibrate, pulsate, or otherwise impart a noticeable tactile signal to the donor's hand. The tactile signal prompts the donor to squeeze the hand gripper, thereby improving venous pressure and avoiding the pressure drops that create Low Flow and No Flow conditions.

Typically, the active gripper of the present invention is itself responsive to a trigger signal from the blood drawing apparatus. The trigger signal may be generated, for example, in response to a measured decrease in line pressure; or in response to a projected decrease in line pressure based on analysis of current and past flow parameters; or at pre-set intervals based on a target gripping frequency; or based on the donor's pattern of actual gripping (e.g., by detecting when the gripper is squeezed and issuing the trigger signal at pre-set times only if the donor has not recently squeezed the gripper). In all of these embodiments, the active gripper and any associated communication means should not restrict the donor's freedom of motion any more than already required by the phlebotomy needle and tubing.

Alternatively, the gripper can be configured for autonomous operation. In this approach, the gripper itself contains circuitry for determining when the tactile signal should be issued. That circuitry may be as simple as a timer, which issues the signal at a pre-set frequency; or may monitor the donor's gripping pattern and issue the tactile signal in response thereto (e.g., if excessive time elapses since the donor's last grip).

The present invention alternatively comprises a method for improving donor blood flow in a blood drawing apparatus through the use of an active donor hand gripper as described above.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
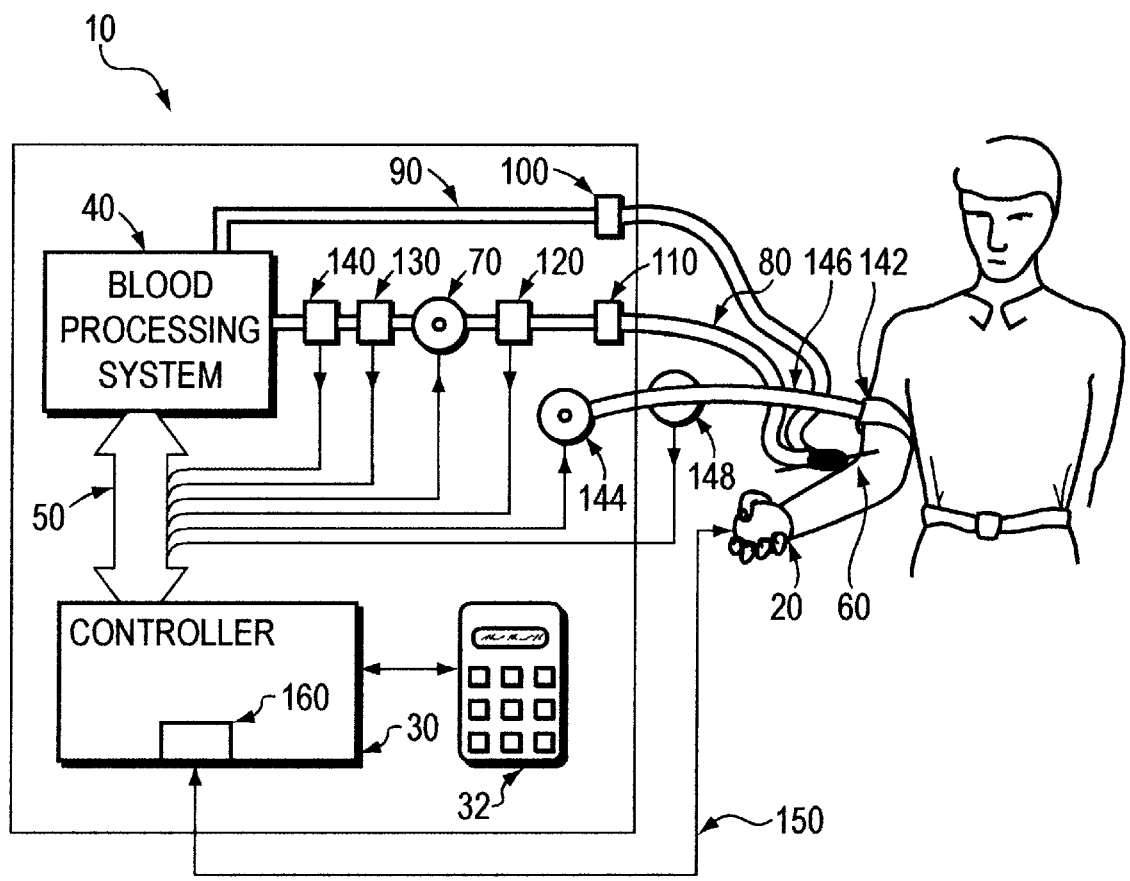
FIG. 1 is a schematic drawing of a blood collection apparatus with an active donor hand gripper.

Refer first to FIG. 1, which illustrates a blood drawing apparatus 10 with an active hand gripper 20. The blood drawing apparatus 10 includes a controller 30 with a keypad 32 or other input/output device for receiving data from an operator, a blood processing system 40 which communicates with the controller 30 through a control bus 50, and a phlebotomy needle 60 that draws whole blood from a donor. A peristaltic pump 70 conducts the drawn blood to the blood processing system 40 through blood compatible tubing 80. An exemplary apheresis apparatus including all of the components mentioned above is described in U.S. Pat. No. 4,416,654, the entire disclosure of which is hereby incorporated by reference.

The blood processing system 40 can implement any of a variety of blood processing protocols as are conventional in the art. Such protocols include simple withdrawal and collection or apheresis directed toward one or more desired blood components. The blood processing system 40 accordingly comprises appropriate storage and separation components to effect the implemented protocol. The blood drawing apparatus 10 may also perform certain functions before whole blood in the blood compatible tubing 80 reaches the peristaltic pump 70, such as mixing with anticoagulants supplied by the blood processing system 40 through anticoagulant tubing 90 and an anticoagulant filter 100, or filtering through a blood filter 110.

The controller 30 will typically monitor blood flow from the donor with at least one pressure monitor 120, at least one line sensor 130, and at least one air detector 140, through signals carried on the control bus 50. The pressure monitor 120 enables the controller 30 to operate the peristaltic pump 70, via the control bus 50, at a rate consistent with the donor's venous pressure at the needle site. The air detector 140 generates a signal based on the presence of fluid in the blood compatible tubing, which is communicated to the controller 30 via the control bus 50, and which the controller 30 uses during operation of the blood drawing apparatus 10. The line sensor 130 determines the turbidity of fluid in the blood compatible tubing 80, thereby facilitating measurement of the concentrations of various blood components. Such sensors, pressure monitors, air detectors, and peristaltic pumps, along with techniques for their automated control, are well characterized in the art.

It is well known to include a pneumatic cuff 142 around the donor's arm to increase venous pressure at the needle site, thereby increasing blood flow rate through the phlebotomy needle 60 and the blood compatible tubing 80. The pneumatic cuff 142 is pneumatically coupled to a compressor 144 through a pneumatic hose 146. The compressor 144 responds to control signals received from the controller 30 over the control bus 50. The blood drawing apparatus 10 also includes a cuff pressure monitor 148 in communication with the controller 10 over the control bus 50. This permits the controller 30 to determine the cuff pressure and send control signals to the compressor 144 in order to most advantageously apply pressure to the donor's arm through the pneumatic cuff 142.

Figure 2:
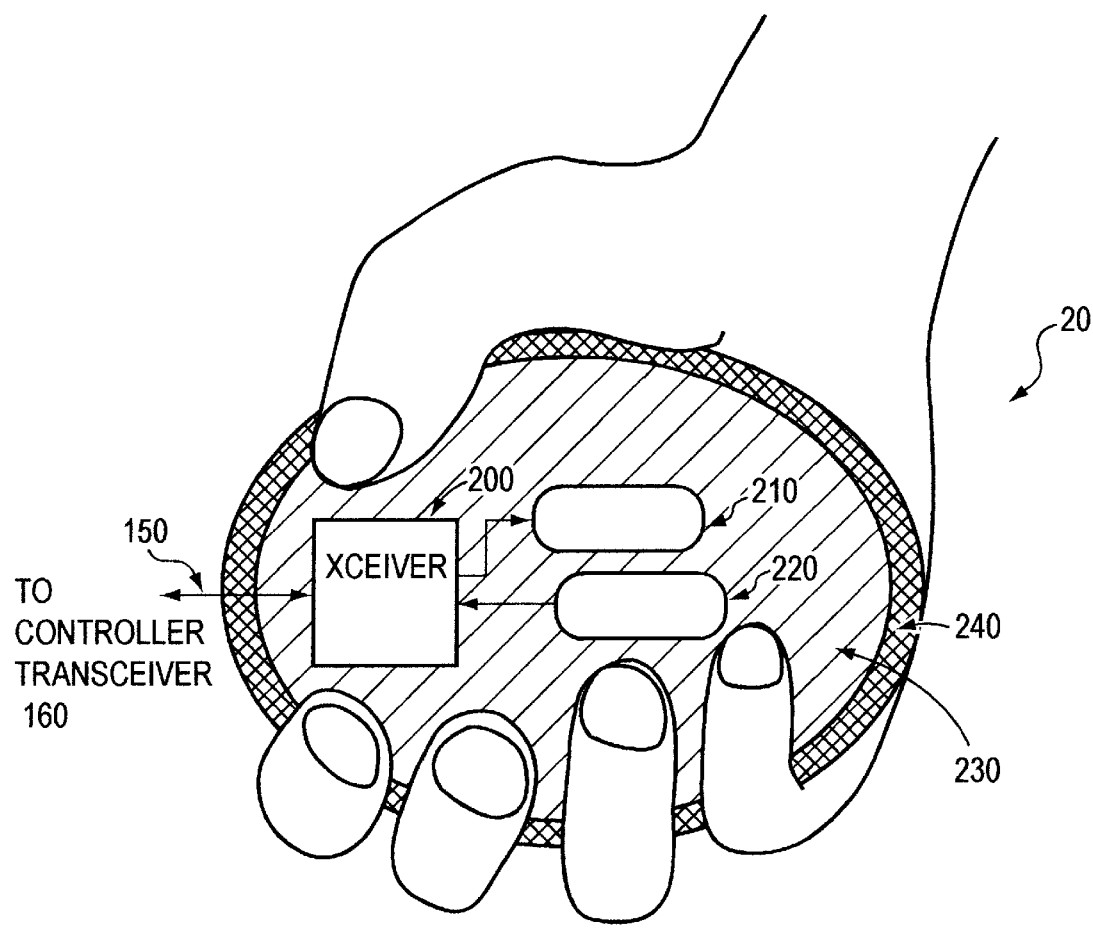
FIG. 2 is a cut-away view of a preferred hand-held electronic device embodiment of the invention.

As shown in FIG. 2, the controller 30 also operates in communication with the hand gripper 20 over a communication link 150 between a controller transceiver 160 (FIG. 1) and a gripper transceiver 200 to periodically deliver an alert signal to the donor. A tactile alert transducer 210 within the hand gripper 20, in response to the alert signal, causes the hand gripper 20 to vibrate, pulsate, or otherwise generate a tactile signal that can be sensed by the donor. The tactile signal should notify the donor when to squeeze his hand in a manner that is noticeable without being intimidating or jarring. The tactile alert transducer 210 may be, for example, an electronic vibrating element. It will be appreciated that a number of means for delivering tactile signals are well known in the art.

In an alternative embodiment, the hand gripper 20 further operates in communication with the controller 30 over the communication link 150 between the gripper transceiver 200 and the controller transceiver 160 (FIG. 1) to indicate when the donor is squeezing the hand gripper 20. In this embodiment, a grip sensing transducer 220 responds to tactile pressure delivered when the donor squeezes the hand gripper 20. The grip sensing transducer 220 converts this stimulus to a grip signal that can be transmitted by the gripper transceiver 200 to the controller transceiver 160 (FIG. 1) over the communication link 150. The grip sensing transducer 220 may be, for example, an embedded microswitch. It will be appreciated that a number of pressure sensitive transducers are well known in the art.

A variety of communication links and transceiver designs, as are well known in the art, may be used in the present invention. For example, the communication link 150 may comprise one or more wires for carrying electrical signals between the controller transceiver 160 (FIG. 1) and the gripper transceiver 200. Alternatively, the communication link 150 may comprise an infrared signal with infrared transceivers in the controller 30 and the hand gripper 20, or an optical signal with appropriate transceivers. The communication link 150 may similarly represent a radio frequency or other wireless communication channel, with the controller transceiver 160 (FIG. 1) and the gripper transceiver 200 containing appropriate circuitry to facilitate two-way communication. Any other communication link 150 known in the art may be used, but it should not restrict the motion of the donor any more than is already required by the phlebotomy needle 60 and the blood compatible tubing 80 of the blood drawing apparatus 10.

In one embodiment, the hand gripper 20 is shaped to fit comfortably within a donor's hand and comprises a casing 230 formed from a pliable medium, such as foamed polyurethane plastic or sponge rubber, that deforms in response to the donor's grip. The casing 230 is also elastic so that it will return to its original shape when the donor's grip loosens. A pliable cover 240 surrounds the casing 230 with a material selected to comfortably engage the donor's hand.

Figure 3:
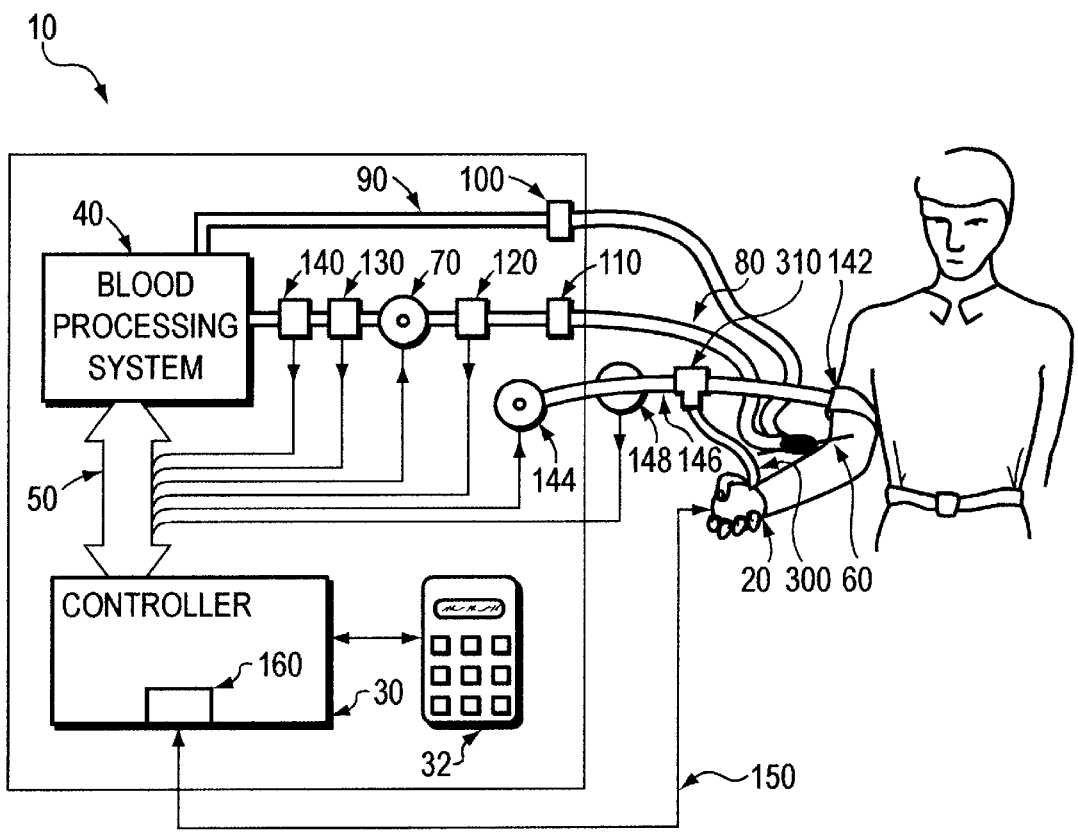
FIG. 3 is a schematic drawing of a pneumatic embodiment of the invention.

As shown in FIG. 3, the hand gripper 20 may alternatively comprise a squeeze bulb pneumatically coupled to the pneumatic cuff 142 through a second pneumatic hose 300 and a pneumatic T-connector 310. In this embodiment, the controller 30 may issue a tactile reminder signal by increasing and decreasing the pressure applied through compressor 144 in rapid succession, thereby creating a series of pneumatic pulses which cause the hand gripper 20 to vibrate or pulsate. Each time the donor squeezes the hand gripper 20, the pneumatic bulb will issue a pulse through the pneumatic hoses 146, 300 to the cuff pressure monitor 148. Thus the controller 30 may monitor grip frequency through electrical signals received over the control bus 50 from the pressure monitor 148. This pneumatic embodiment of the hand gripper 20 comprises a pliable cover 240 of polypropylene, polyamide, neoprene, or other pliable plastic material with a casing 230 of fluid or gas substantially filling the interior space.

In an apheresis procedure, whole blood is drawn from a donor during a draw process. During this process, the controller 30 implements a control algorithm to determine when the tactile alert transducer 210 should prompt the donor to squeeze the hand gripper 20. In a simple form, the control algorithm applies a deterministic formula such as prompting the donor to squeeze once every 30 seconds, or at some other rate. More sophisticated algorithms are also possible, and may employ one or more of the inputs available to the controller 30 through the control bus 50 and the controller transceiver 160.

For example, the control algorithm can receive as an input the donor squeeze rate, as established by signals received by the controller 30 from the grip sensing transducer 220, and cause the controller 30 to deliver an alert signal to the tactile alert transducer 210 only when the donor squeeze rate falls below a predetermined level; or the control algorithm can receive as an input the donor's venous pressure, as detected by the pressure monitor 120 and transmitted to the controller 30 over the control bus 50, and cause the controller 30 to deliver an alert signal when the pressure falls below a predetermined level. In a still more sophisticated control algorithm, the controller 30 can monitor inputs from one or more of the pressure monitor 120, the line sensor 130, the air detector 140, the cuff pressure monitor 148, and the grip sensing transducer 220, and use these inputs to predict future blood flow rate patterns, thereby preemptively delivering alert signals to avoid expected drops in donor's venous pressure. The goal in all of these approaches is to achieve an adequate donor blood flow rate throughout the blood drawing process.

Figure 4:
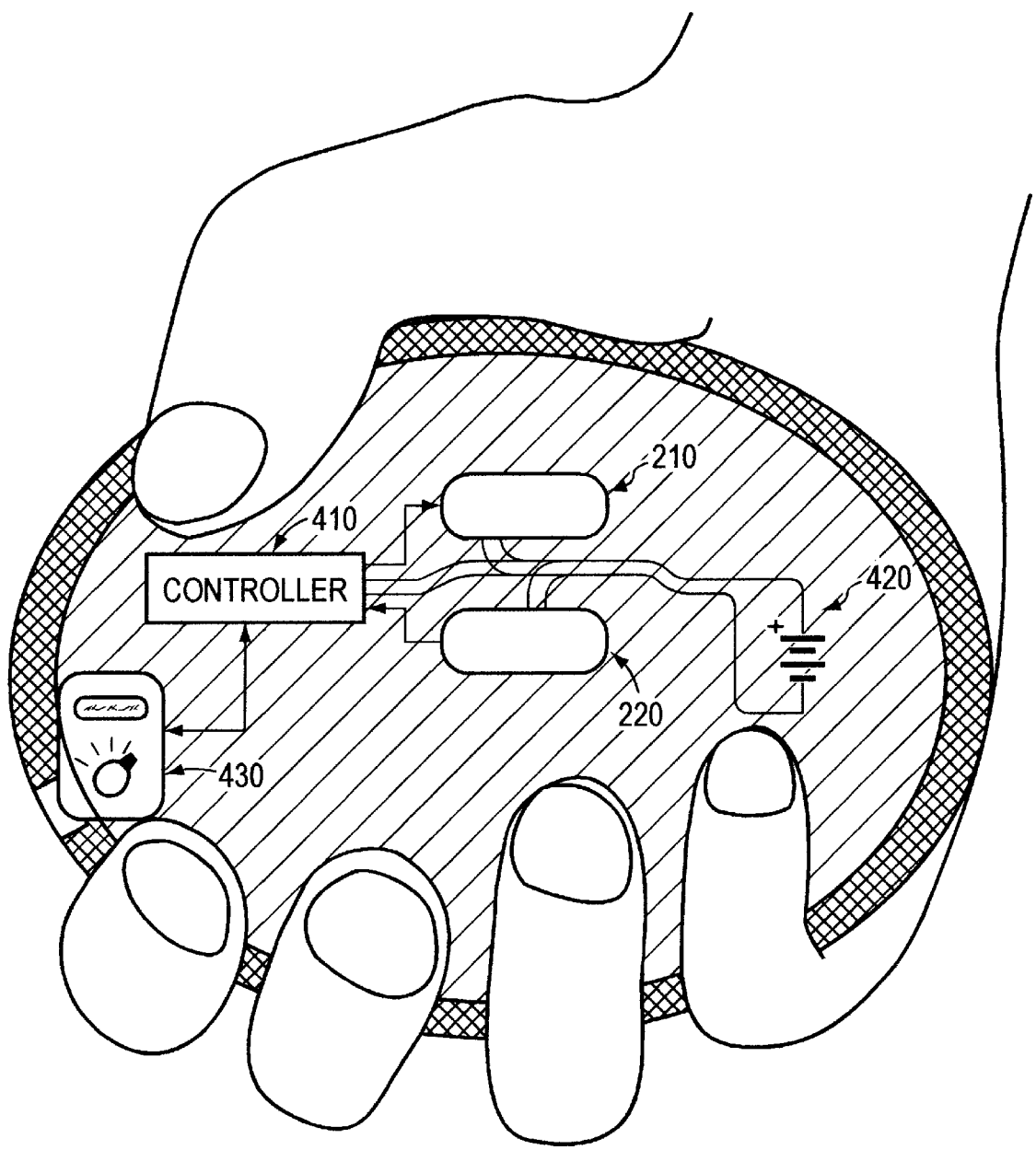
FIG. 4 is a cut-away view of a fully autonomous embodiment of the invention.

As shown in FIG. 4, another embodiment of the present invention comprises an autonomous hand gripper 400. In this embodiment, the autonomous hand gripper 400 contains an autonomous controller 410, a power source 420, a grip sensing transducer 220, and a tactile alert transducer 210.

The autonomous controller 410 can receive input from the grip sensing transducer 220. In an operation substantially similar to that described above for the hand gripper 20, the autonomous controller 410 will generate an alert signal that is transmitted to the tactile alert transducer 210 when the donor should squeeze the autonomous hand gripper 400.

During a blood drawing process, the autonomous controller 410 implements a control algorithm to determine when the tactile alert transducer 210 should prompt the donor to squeeze the autonomous hand gripper 400. The control algorithm may apply a deterministic formula such as prompting the donor to squeeze the hand gripper 400 once every 30 seconds, or at some other rate. Alternatively, the controller may receive as an input the donor squeeze rate, as established by a signal received by the controller 410 from the grip sensing transducer 220, and cause the controller 410 to deliver an alert signal to the tactile alert transducer 210 only when the donor squeeze rate falls below a predetermined level. The hand gripper 400 preferably includes an input/output device 430, such as a dial and a digital display, connected to the controller 410 permitting an operator to select a threshold squeeze rate.

The autonomous hand gripper 400, the autonomous controller 410, the grip sensing transducer 220, the tactile alert transducer 210, and the input/output device 430 may all be implemented with a variety of means that are well known in the art, all of which has been discussed in the context of the hand gripper 20. The autonomous embodiment of the hand gripper 400 further comprises a power source 420 within the hand gripper 400. The autonomous controller 410, the grip sensing transducer 220, and the tactile alert transducer 210 receive power from the power source 420 within the autonomous hand gripper 400 so that the autonomous hand gripper 400 can operate independently from the blood drawing apparatus 10.

The functions of the present invention are implemented on the foregoing basic platform through suitable configuration of the controller 30 or the autonomous controller 410. The controller 30 or the autonomous controller 410 may be implemented, for example, using a programmable, single-chip microcomputer or microcontroller which incorporates analog-to-digital converters for transforming the signals from the various analog sensors into digital signals that may be processed by the microcomputer. Alternatively, the circuitry may be implemented in other electronic forms such as an application specific integrated circuit or discrete electronics.

It should be emphasized that the present invention may be usefully practiced in conjunction with virtually any type of blood collection system, regardless of the ultimate product or products obtained. It will therefore be seen that the foregoing represents an improved and effective approach to blood collection. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. An active donor hand gripper for improving the blood flow rate in a blood drawing apparatus, the hand gripper comprising:

(a) a deformable body;

(b) means for periodically issuing a tactile reminder signal to alert a donor to squeeze the body;

(c) means for generating a grip signal when the body is squeezed; and (d) a controller coupled and responsive to the grip signal for determining a donor squeeze rate and activating the tactile reminder signal issuing means when the donor squeeze rate falls below a predetermined threshold.

2. The apparatus of claim 1 wherein the controller is embedded in the hand gripper.

3. The apparatus of claim 1 further comprising a communication link over which the means for issuing a tactile reminder signal and the means for generating a grip signal communicate with the controller.

4. The apparatus of claim 3 wherein the communication link comprises means for transceiving electrical signals over electrically conductive wire between the hand gripper and the controller.

5. The apparatus of claim 3 wherein the communication link comprises means for transceiving infrared signals between the hand gripper and the controller.

6. The apparatus of claim 3 wherein the communication link comprises means for transceiving radio frequency signals between the hand gripper and the controller.

7. The apparatus of claim 3 wherein the communication link comprises means for transceiving optical signals between the hand gripper and the controller.

8. The apparatus of claim 3 wherein the hand gripper comprises a pneumatic squeeze bulb and the communication link comprises a compressor and a pneumatic pressure sensor in pneumatic communication with the pneumatic squeeze bulb, the tactile reminder signal and the grip signal being pneumatic pulses.

9. The apparatus of claim 1 wherein the hand gripper is configured to fit within a donor's hand and comprises a deformable case.

10. A method for improving donor blood flow in a blood drawing apparatus comprising the steps of:

(a) providing a donor with a hand-held gripping device having an electronic vibrating element;

(b) determining a donor squeeze rate of the gripping device;

(c) causing the electronic vibrating element to issue a tactile reminder signal to the donor, thereby stimulating the donor to squeeze the gripping device when the donor squeeze rate falls below a predetermined threshold.

11. The method of claim 10 further comprising the steps of:

(a) determining a squeeze rate for the hand gripper; and (b) issuing the tactile reminder signal when the squeeze rate falls below a predetermined level.

12. The method of claim 10 further comprising the steps of:

(a) determining a donor venous pressure; and (b) issuing the tactile reminder signal when the donor venous pressure falls below a predetermined threshold.

13. A system for improving the blood flow rate in a blood drawing apparatus, the system comprising:

(a) a hand gripper comprising:

(i) means for vibrating the hand gripper in response to a vibrate signal; and (ii) means for generating a grip signal when the hand gripper is squeezed; and (b) a controller associated with the blood drawing apparatus coupled and responsive to the grip signal and comprising:

(i) means for receiving the grip signal from the hand gripper;

(ii) means for receiving a donor venous pressure signal from the blood (iii) means for receiving a line sensor signal from the blood drawing apparatus;

(iv) means for receiving a cuff pressure signal from the blood drawing apparatus; and (v) means for generating the vibrate signal in response to at least one of the grip signal, the donor venous pressure signal, the line sensor signal, and the cuff pressure signal.

14. An active donor hand gripper for improving the blood flow rate in a blood drawing apparatus, the hand gripper comprising:

(a) a deformable body;

(b) an electronic vibrating element mounted to the deformable body, the vibrating element configured to issue a tactile reminder signal to alert a donor to squeeze the body; and (c) a controller mounted to the deformable body and coupled via a communications link to the vibrating element, the controller configured to cause the vibrating element to issue the tactile reminder signal in response to one of a donor squeeze rate of the deformable body falling below a predetermined squeeze rate threshold and a donor venous pressure value falling below a predetermined venous pressure threshold.

15. The active donor hand gripper of claim 14 wherein the communication link comprises means for transceiving electrical signals over electrically conductive wire between the hand gripper and the controller.

16. The active donor hand gripper of claim 14 wherein the communication link comprises means for transceiving infrared signals between the hand gripper and the controller.

17. The active donor hand gripper of claim 14 wherein the communication link comprises means for transceiving radio frequency signals between the hand gripper and the controller.

18. The active donor hand gripper of claim 14 wherein the communication link comprises means for transceiving optical signals between the hand gripper and the controller.

19. The hand gripper of claim 14 wherein the hand gripper is configured to fit within a donor's hand and comprises a deformable case.

20. The active donor hand gripper of claim 14 further comprising a grip signal generating means mounted to the hand gripper, wherein the controller further comprises:

(a) means for receiving the grip signal from the grip signal generating means; and (b) means for determining the donor's squeeze rate based on the received grip signal.

21. The active donor hand gripper of claim 14, the controller further comprising:

(a) means for receiving a pressure signal from the blood drawing apparatus indicative of a donor venous pressure at a phlebotomy needle site; and (b) means for activating the electronic vibrating element when the controller determines that the donor venous pressure is inadequate.

22. A method for improving donor blood flow in a blood drawing apparatus comprising the steps of:

(a) providing a donor with a hand-held gripping device having means for issuing a tactile reminder signal to the donor;

(b) sensing the donor's actual squeeze rate of the gripping device; and (c) periodically causing the gripping device to issue a tactile reminder signal to the donor when the actual squeeze rate falls below a predetermined target squeeze rate, thereby stimulating the donor to squeeze the gripping device.

23. The method of claim 22 wherein the step of issuing a tactile stimulus comprises the step of pneumatically vibrating the hand gripper.

24. The method of claim 22 wherein the step of issuing a tactile stimulus comprises the step of electronically vibrating the hand gripper.

25. The method of claim 22 further comprising the steps of:

(a) determining a donor venous pressure; and (b) issuing the tactile reminder signal when the donor venous pressure falls below a predetermined threshold, thereby stimulating the donor to squeeze the gripping device.

26. An active donor hand gripper for improving the blood flow rate in a blood drawing apparatus, the hand gripper comprising:

(a) a deformable body;

(b) means for periodically issuing a tactile reminder signal to alert a donor to squeeze the deformable body;

(c) means for receiving a pressure signal from the blood drawing apparatus indicative of a donor venous pressure at a phlebotomy needle site; and (d) a controller operatively coupled to the pressure signal and configured to generate the tactile reminder signal when the donor venous pressure falls below a predetermined threshold.

* * * * *